US006989007B2

(12) United States Patent
Shadduck

(10) Patent No.: US 6,989,007 B2
(45) Date of Patent: *Jan. 24, 2006

(54) DEVICES AND TECHNIQUES FOR TREATING GLAUCOMA

(75) Inventor: John H Shadduck, Tiburon, CA (US)

(73) Assignee: Solx, Inc., Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 10/765,482

(22) Filed: Jan. 27, 2004

(65) Prior Publication Data

US 2004/0186534 A1    Sep. 23, 2004

Related U.S. Application Data

(63) Continuation-in-part of application No. 09/790,242, filed on Feb. 21, 2001, now Pat. No. 6,682,523.

(51) Int. Cl.
*A61B 18/18*    (2006.01)

(52) U.S. Cl. .................. 606/4; 606/5; 607/88; 128/898
(58) Field of Classification Search ................ 606/4–6; 607/88, 89; 128/898
See application file for complete search history.

(56) References Cited

U.S. PATENT DOCUMENTS

| | | | |
|---|---|---|---|
| 4,391,275 A * | 7/1983 | Fankhauser et al. ........... | 606/4 |
| 5,259,380 A | 11/1993 | Mendes et al. | |
| 5,372,595 A | 12/1994 | Gaasterland et al. | |
| 5,549,596 A * | 8/1996 | Latina ........................... | 606/4 |
| 6,059,772 A * | 5/2000 | Hsia et al. ..................... | 606/4 |
| 2004/0039378 A1 * | 2/2004 | Lin ................................ | 606/6 |

OTHER PUBLICATIONS

Manns, Fabrice et al. "Qualitative optical-thermal model of argon, selective, and mocrosecond infrared laser trabeculoplasty", pp. 1-6.
Sliney, David H. et al. "The Evaluation of Laser Hazards", American Industrial Hygiene Association, Sep.-Oct. 1968, pp. 425-431.
Jacques, Steven L. et al., "The Melanosome: Threshold Temperature For Explosive Vaporization and Internal Absorption Coefficient During Pulsed Laser Irradiation", Photochemistry and Photobiology, 1991, pp. 769-775, vol. 53, No. 6, Pergamon Press.
Jacques, Steven L. et al., "Internal absorption coefficient and threshold for pulsed laser disruption of melanosomes isolated from retinal pigment epithelium", SPIE, pp. 468-477, vol. 2681.
Goldman, Leon, "The Skin", Arch Environ Health, Mar. 1969, pp. 1-3, vol. 18.
Prota, Giuseppe et al., "The Chemistry of Melanins and Related Metobolites", The Pigmentary System, Chapter 24, pp. 307-332.
"Selecta duet", 2002, pp. 1-6, Lumenis group of companies.

* cited by examiner

Primary Examiner—A. Farah
(74) Attorney, Agent, or Firm—Maine & Asmus

(57) ABSTRACT

A system for non-invasive treatment of a patient's trabecular meshwork to treat primary open-angle glaucoma. The system and technique applies energy directly to media within clogged spaces in a patient's trabecular meshwork to increase aqueous outflow facility by (i) localization of microimplantable bodies carrying a selected exogenous chromophore, such as particles with a gold surface, in deeper regions of the trabecular meshwork, and (ii) irradiation of the microimplantables with a selected coherent wavelength having a power level and pulse duration that is strongly absorbed by the surfaces of the microimplantables.

11 Claims, 8 Drawing Sheets

DEVICES AND TECHNIQUES FOR TREATING GLAUCOMA

CROSS-REFERENCE TO RELATED APPLICATIONS

This application is a Continuation-in-Part of U.S. patent application Ser. No. 09/790,242 filed Feb. 21, 2001 titled Devices and Techniques for Treating Trabecular Meshwork now, U.S. Pat. No. 6,682,523.

BACKGROUND OF THE INVENTION

1. Field of the Invention

The present invention relates to the field of glaucoma therapy and more particularly to a laser-based system and technique for treating a patient's obstructed outflows pathways in the eye to enhance aqueous outflows and thereby lower intraocular pressure. The system and method introduces uniformly dimensioned nanoparticles into meshwork spaces to provide photoabsorption of a selected wavelength to thereby deliver energy directly to media and trabecular cords of the trabecular meshwork.

2. Description of Related Art

Glaucoma is a general term given to a group of debilitating eye diseases that afflict approximately 1%–2% of the U.S. population and an estimated 67 million people worldwide. In the U.S, the incidence of glaucoma rises with age to over 6% of the Caucasian population 75 years and older, and about 11% of the population of African descent 75 years and older. Glaucoma represents a significant health care issue, with millions of people worldwide at risk of vision loss.

The principal sign of glaucoma is elevated intraocular pressure (IOP) that ultimately can damage the optic nerve and result in impairment to, or loss of, normal visual function. Aqueous humor aq is the clear nutrient fluid that circulates within the anterior chamber ac of an eye to nourish ocular tissues. The aqueous aq is produced by the ciliary body cb and is drained through the trabecular meshwork tm and Schlemm's canal sch (see FIG. 1A). In a glaucoma condition, drainage of aqueous through the trabecular meshwork tm is insufficient to balance aqueous production, and therefore fluid intraocular pressure can be elevated and eventually damage the optic nerve.

Primary open-angle glaucoma is the most prevalent open-angle glaucoma in the U.S. representing approximately 37% of total U.S. cases, or about 1.2 million people, with an estimated 63,000 new cases annually. The pathophysiological mechanisms underlying primary open-angle glaucoma are not fully understood. It is believed that one or more factors play a role, for example, (i) that as a patient ages, the trabecular meshwork undergoes biostructural changes and loses its ability to regulate outflows, or (ii) that naturally elevated IOP levels can be tolerated initially, but after a long period begin to cause irreversible damage.

Another form of ocular hypertension is caused by exfoliation syndrome or exfoliation glaucoma. In this condition, the iris rubs against the lens and dislodges white flakes from the lens surface that are carried by the aqueous humor into the trabecular meshwork. It is believed that the exfoliated flakes build up in the trabecular meshwork and block outflow facility, eventually leading to a rise in IOP and full-blown glaucoma. This type of exfoliation glaucoma accounts for approximately 20% of total U.S. glaucoma cases or about 660,00 people. An estimated 34,000 new cases are diagnosed annually in the U.S.

Pigmentary glaucoma is caused by pigment dispersion syndrome wherein abrasive contact between the iris and lens sheds pigment into the anterior chamber and aqueous humor. The pigment again can clog the trabecular meshwork and increase IOP. Pigmentary glaucoma accounts for approximately 3% of total U.S. glaucoma cases or about 100,000 people with an estimated 5,000 new cases per year.

The ability of the trabecular meshwork in filtering aqueous flows plays a central role in many forms of glaucoma. The meshwork consists of about 25 layers of perforated trabecular sheets ($ts_1 \ldots ts_{25}$) around the filtration angle of the anterior chamber ac, having a width of about 1,000 $\mu$m to 1,500 $\mu$m (1.0 mm. to 1.5 mm.) in a circumference ranging from 35,000 to 40,000 $\mu$m (see FIGS. 1A–1B). FIG. 1C shows an enlarged micrograph of trabecular cords and openings. FIG. 1E is a representation of the endothelial layer el of a trabecular cord tc or beam wherein its core comprises predominantly collagen microfibrils. FIG. 1D illustrates that each successively deeper trabecular sheet ts of the meshwork has smaller openings or pores p between trabecular cords tc than more superficial trabecular sheets. Further, the intrasheet spacing iss diminishes between successively deeper trabecular sheets ts. The meshwork thus serves as a filtration mechanism wherein cellular detritus and other debris in the aqueous flow is captured before it passes into Schlemm's canal sch wherein the outflows are carried away from the anterior chamber. FIG. 1D includes a graphic representation of exfoliated detritus indicated at d accumulating within spaces in the meshwork that are believed responsible for reducing outflow facility through the meshwork and for collapsing intrasheet spacing.

Various laser therapies have been developed or proposed for treating a patient's trabecular meshwork. These laser approaches rely on trans-corneal irradiation of a series of spots on the surface of meshwork tm exposed to the anterior chamber. The ophthalmologist utilizes a goniolens to direct the laser beam to strike exposed trabecular sheets at an oblique angle. For example, argon laser trabeculoplasty (ALT) and selective laser trabeculoplasty (SLT) have been tested and compared in several trials. ALT was introduced in the 1980's and uses an argon laser operating at a wavelength (A) range of about 512 nm with a pulse duration of about 0.10 second to irradiate a series of about 50 spots only around 180° of the meshwork. The more recently developed trans-corneal laser approach, called SLT, uses a short-pulse 532 nm laser with pulse duration of 3–10 nanoseconds and energy levels that range from 0.60 mJ to 1.20 mJ. This approach was disclosed by Latina in U.S. Pat. No. 5,549,596. Yet another trans-corneal laser approach was disclosed by Hsia et al. in U.S. Pat. No. 6,059,772. Hsia disclosed three experimental trials on a limited set of human patients using an 800 nm laser beam with microsecond pulse durations, and varied energy levels. TABLE A below compares the laser parameters used in the various approaches, arranged in order of increasing wavelengths ($\lambda$).

TABLE A

| | $\lambda$ | Pulse Duration | Power | Beam Size |
| --- | --- | --- | --- | --- |
| ALT | 514 nm | 0.1 second (100 ms) | various powers settings | 50 $\mu$m |
| SLT | 532 nm | 3 ns–10 ns | 0.6–1.2 mJ/pulse | 300–400 $\mu$m |
| Hsia et al. | 800 nm | 1 microsecond | 30–80 mJ/pulse | 100–200 $\mu$m |

A recent series of articles provides a comparative evaluation of ALT and SLT and investigates the mechanisms of action that underlie ALT and SLT to lower intraocular pressure (see *Ocular Surgery News*, Mar. 1, 2000). The results of these evaluations also can be instructive as to the probable mechanisms of action underlying the laser approach, if eventually proven under FDA regulatory schemes, that was proposed by Hsia in U.S. Pat. No. 6,059,772.

The ALT and SLT approaches use very similar wavelengths—514 nm for ALT vs. 532 nm for ALT. Still, as reported by Dr. J. Alvarado, the laser-tissue interactions in trabecular meshwork tissues of glaucoma patients differ markedly between ALT and SLT. (See Alvarado, J. A., *Mechanical and Biological Comparison of ALT and SLT; Ocular Surgery News*, Mar. 1, 2000). The ALT treatment modality produces a discrete burn or photocoagulation-type injury in trabecular sheets that are impacted by the laser irradiation. The damage is clearly visible to the ophthalmologist through a slit-lamp biomicroscope. In contrast to ALT, the SLT method produces no laser burns—the trabecular meshwork appears undamaged and without tissue reaction to the incident radiation. Dr. Alvarado stated that "[d]espite differences in the interaction of the laser light with the treated tissues, early clinical outcome comparisons of SLT and ALT have shown that the treatments are similar in the capacity to lower the intraocular pressure (IOP) of glaucoma patients." Id. at p. 1. From TABLE A, it is readily apparent that the main difference between ALT and SLT is the pulse duration and the hence the energy delivered per pulse to the targeted tissue volume (e.g., fluence in $J/cm^2$). The thermal relaxation time between laser pulses also is of critical importance, but was not discussed in detail in the Alvarado article referenced above.

In both ALT and SLT, the light emissions interact with the principal chromophore found in the trabecular meshwork, which in this case comprises melanin granules in the cytoplasm of endothelial cells lining the meshwork. While the ALT and SLT wavelengths target melanin, the pulse duration of SLT is so brief (in the range of 3 ns to 10 ns) that the energy absorption within, or vaporization of, the melanin polymer does not transfer significant thermal energy to surrounding connective tissue (i.e., collagen microfibrils in the trabecular cords) or other non-melanin containing cells. In contrast, ALT delivers very substantial amounts of energy in long 100 ms pulses to chromophore granules, which thus results in the transfer of thermal effects throughout the trabecular cord. The thermal relaxation time for such tissue in considered equal to about 1 ms—so that the ALT pulse duration alone exceeds the thermal relaxation time by a factor of 100. One aspect of the laser-tissue interaction underlying ALT that lowers IOP is related to the coagulation and shrinkage of connective tissues (i.e., collagen microfibrils) at the laser impact site. It is proposed that the net effect of shrinkage of trabecular cords and trabecular sheets by laser coagulation is to stretch and open trabecular spaces within meshwork portions proximate to the totally coagulated or melted tissues, thereby providing improved aqueous outflows through some portions of the meshwork. However, such locally beneficial effects come at the expense of "melting" other adjacent portions of the meshwork structure and even displacing Schlemm's canal. Since ALT causes such substantial biostructural alterations, the procedure is not considered to be repeatable over the patient's lifetime.

A second factor is proposed to play a role in ALT to improve outflows, which relates to macrophage recruitment. Small numbers or monocytes are continuously circulating within aqueous flows that exit the eye through the meshwork tm and Schlemm's canal. It is believed that these monocytes are activated and transformed into macrophages in response to a tissue injury as part of the body's wound healing response—as when an ALT incident beam strikes the meshwork causing damage around the absorbing or exploding chromophore. (See Alvarado, J. A., Murphy, C. G., *Outflow obstruction in pigmentary and primary open angle glaucoma, Arch Ophthalmol.* 110, 1769–1778 (1992)). Following ALT, it was observed that numerous macrophages engulfed the melanin granules and remnants thereof in the meshwork and cleared the detritus from the meshwork tissues by circulation through Schlemm's canal.

In SLT, a similar mechanism relating to macrophage recruitment is believed to predominate to improve aqueous outflows through the meshwork, thus lowering intraocular pressure. In animal studies, it was observed that an SLT treatment caused a five-fold to eight-fold increase in the number of monocytes and macrophages in the meshwork. Dr. Alvarado proposed that SLT-induced injury to meshwork cells caused by photon absorption in melanin results in the release of factors and chemoattractants that recruit macrophages in a manner similar to that observed in ALT treatments. (See Alvarado, J. A., *Mechanical and Biological Comparison of ALT and SLT; Ocular Surgery News*, p. 3, Mar. 1, 2000). The SLT treatment parameters selected by the author (Latina) of U.S. Pat. No. 5,549,596 resulted from testing 532 nm and 1064 nm q-switched Nd:Yag lasers and an argon (ALT) laser in trabecular cell cultures having melanin pigments introduced therein. It was found that ALT irradiation at several ms pulse durations would ablate cells proximate to the absorbing melanin pigments. Latina thereafter selected low fluences (obtainable with very short pulse q-switched Nd:Yag laser) to allow photon absorption by the chromophore and subsequent thermal relaxation (heat dissipation) between laser pulses to prevent gross disruption of other cells in the culture. (See Latina, M. A., *Underlying Principles and Pre-Clinical Studies of SLT; Ocular Surgery News*, Mar. 1, 2000). By this means, the ns pulses shown in TABLE A were selected for meshwork treatments which later became known as SLT.

In summary, the data indicates that laser-induced alteration of connective tissue macromolecules (i.e., shrinkage of trabecular cords) caused by the absorption and conduction of thermal effects throughout trabecular beam occurs in ALT—but not SLT. However, ALT and SLT both utilize a second mechanism for facilitating outflows—that is, the recruitment of macrophages that clean detritus from the meshwork following ALT and SLT incident radiation that is induced by the body's wound healing response.

Now turning to the treatment modality suggested by Hsia in U.S. Pat. No. 6,059,772, it is unknown whether the clinical experiments disclosed by Hsia will lead to commercialization of 800 nm lasers for specific meshwork treatments. However, it seems possible to predict with a reasonable level of confidence the exact nature of the laser-tissue interaction that will result from Hsia's treatment parameters, since the parameters are effectively bracketed by the ALT and SLT modalities of treatment.

In order to compare Hsia's approach to the well-documented ALT and SLT approaches, it first is necessary to describe in more detail the only true laser-tissue interaction that can serve as a therapeutic mechanism in meshwork treatments. All the methods listed in TABLE A rely on laser irradiation that is absorbed by the only chromophore (other than water) in the trabecular meshwork: melanin granules which are found in endothelial layers of the trabecular cords. Thus, by characterizing this chromophore's absorption characteristics in more detail, the mechanism of treating the meshwork can be understood to flow directly from the initial absorption, explosion or vaporization of melanin target.

Melanin is a complex material as it relates to photon absorption. The melanins formed from natural sources fall into two general classes: (i) eumelanin which is characterized as a brown to black insoluble composition (e.g., found in the retina, black hair, skin and certain other tissue epithelial and endothelial layers) and (ii) pheomelanin which is characterized as a yellow to reddish-brown alkali-soluble material (e.g., found in red hair). It is believed that naturally occurring melanin found in the trabecular meshwork falls only within the eumelanin class.

Such eumelanins are considered to be polymers that form links to other proteins. However, the details of the polymerization and the role of protein linkages in the natural melanin complex are not known. It is believed that insoluble melanins are highly polymeric cross-linked structures consisting of several hundred monomeric units. (See Prota, G., D'Ischia, M., Napolitano, A., *The chemistry of melanins and related metabolites*, in *The Pigmentary System*, ed. J. J. Nordlund et al., Oxford University Press, (1988)). Melanin granules are synthesized enzymatically at approximately 10 nm granular sites about the interior of a melanosome. A melanosome consists of an approximately 1 $\mu$m diameter organelle that can contain widely varied amounts of melanin. For example, the melanosomes of the retinal pigmented epithelium have a dense concentration of melanin. In contrast, cutaneous melanosomes are variable and may have as little as 10% of the melanin concentration of retinal melanosomes, while others can be altogether devoid of melanin. Moreover, the volume fraction ($f_v$) of melanosomes in a particular epithelial layer, such as the cutaneous epidermis or retinal epithelium, varies greatly. The average absorption coefficient of a targeted volume depends on both the melanosomal $\mu_a$ (absorption coefficient) and the volume fraction ($f_v$) of melanosomes in target. For example, in skin, the volume fraction of melanosomes is estimated at 1–3% for light skinned Caucasians; 11–16% for well-tanned Caucasians and Mediterraneans, and 18–43% for darkly pigmented Africans. It is believed that the trabecular cord epithelial layers carry a very small volume fraction ($f_v$) of melanosomes, as evidenced by the fact that the structure is substantially translucent when viewed through a biomicroscope (see graphic representation of FIG. 1D).

Next, it is necessary to understand the average absorption coefficient $\mu_a$ (cm$^{-1}$) for the interior of a melanosome that carries melanin granules or particles. In other words, the degree of in vivo photothermal or photomechanical effects in a targeted melanosome caused by a pulse of laser radiation comprises the critical mechanisms for evaluating any form of laser treatment of the trabecular meshwork. (In a collateral field, the amount of photons absorbed by a melanosome also can create oxidative reactions that are catalyzed by melanosomes exposed to blue or ultraviolet wavelengths).

FIG. 2 is a graphical representation of the $\mu_a$ of melanosomes based on several studies. Some studies investigated the threshold pulsed laser radiant exposure that causes vaporization of melanosomes to calculate the $\mu_a$. For example, Jacques and McAuliffe used such vaporization to measure the $\mu_a$ of melanosomes in ex vivo human skin specimens, as well as literature data from similar in vivo measurements (see Jacques, S. L., McAuliffe, D. J., *The melanosome: threshold temperature for explosive vaporization and internal absorption coefficient during pulsed laser irradiation*. Photochem. Photobiol. 53:769–775 (1991)). In another study, Jacques, et al. used vaporization to measure the $\mu_a$ of melanosomes isolated from bovine retinal pigmented epithelium (see Jacques, S. L., Glickman, RD., Schwartz, J. A., *Internal absorption coefficient and threshold for pulsed laser disruption of melanosomes isolated from retinal pigment epithelium*. SPIE Proceedings 2681: 468–477 (1996)). The absorption coefficient $\mu_a$ of the melanosome inte of FIG. 2 also includes data based on optical measurements (see Goldman, L., *The Skin, Arch. Environmental Health*, 18:435, (1969); Sliney, D. H., Palmisano, W. A., *The evaluation of laser hazards, AIHA Journal* 20: 425 (1968)). To repeat, the concentration of melanin within melanosomes is quite variable, with ten-fold variation to be expected. However, the general shape of the melanosome absorption spectrum is approximated in FIG. 2 (see similar graph provided by S. Jacques at http://omlc.ogi.edu/spectra/melanin/jacques.mcauliffe.gif).

What is clear from the melanosome absorption coefficient and spectrum of FIG. 2 is that melanin has no sharp peaks and valleys common to some chromophores, such as when some close together wavelengths are highly absorbing and others are highly non-absorbing. In fact, the slope of the absorption spectrum FIG. 2 is smooth with somewhat higher absorption coefficients (lesser depth of photon penetration) at shorter wavelengths. The absorption spectrum of FIG. 2 shows that the 514 and 532 nm wavelengths of ALT and SLT, respectively, will be absorbed similarly for any given energy level. For this reason, at least one investigator thus far has opined that ALT would have an effect similar to SLT at lower power settings (see Alvarado, J. A., *Mechanical and Biological Comparison of ALT and SLT; Ocular Surgery News*, p. 3, Mar. 1, 2000). In fact, it seems clear from TABLE A—and the very slight difference in $\mu_a$ of melanin at 514 and 532 nm—that there can be no difference between ALT and SLT other than fluence (e.g., defined in mJ/cm$^2$ of irradiated tissue).

Turning now to the question of the laser-tissue interaction proposed by Hsia in U.S. Pat. No. 6,059,772, it can be seen from FIG. 2 that laser irradiation at 800 nm will be substantially absorbed within melanosome organelles, although such a wavelength can penetrate more deeply in the melanosome than will 532 nm wavelengths. However, any series of tests of 800 nm irradiation of melanosomes at varied power levels should be able to reproduce the thermal effects of SLT—or ALT. In fact, the power levels (and hence fluences) proposed as effective by Hsia are higher than SLT power levels, and appear lower than ALT power levels. The laser tissue interactions caused by energy delivery within the Hsia parameters, when factoring in $\mu_a$, spot size and pulse duration, seem effectively bracketed on the high side by ALT and the low side by SLT. Thus, the results of meshwork treatments under Hsia's parameters will be a laser-tissue interaction again bracketed by the proposed ALT and SLT mechanisms of action: (i) at a moderate energy fluences, the energy deposition in, and explosion of, some melanosomes will induce the body's wound healing response to increase monocyte\macrophage activity; and (ii) at higher energy fluences, the explosion or vaporization of melanosomes can be expected to alter the ultrastructure of the trabecular beams due to heat conduction throughout the beams.

According the Hsia disclosure, the energy delivery parameters at 800 nm shown in TABLE 1 apparently result in treatment effects similar to SLT—that is, no gross damage to meshwork cells or to the trabecular cord ultrastructure. The Hsia disclosure further describes a "non-preferred" set of treatment parameters tested in ex vivo experiments at higher energy levels (20 to 100 mJ with 100–200 micron spot sizes). In those experiments, the 800 nm laser irradiation caused significant thermally-induced modifications of meshwork ultrastructure, up to and including the ablation of holes in the meshwork—which is equivalent to ALT at high power levels. Thus, assuming the Hsia treatment parameters shown in TABLE 1 result in lowered IOP, the mechanisms of action almost certainly are the same as those underlying the ALT and SLT treatment modalities—simply depending on actual fluences selected to deliver to meshwork endothelial layers by modulation of power and spot sizes.

It is reasonable to question yet another aspect of the Hsia treatment parameters. The Hsia disclosure provides for relatively long (e.g., 1 ms) pulse durations at the wavelength of 800 nm that is absorbed by water far more greatly than ALT and SLT wavelengths. Water makes up about 90–95% of cornea tissue and substantially all of the aqueous humor. Transcorneal irradiation via a goniolens requires beam transmission though this predominantly water media before reaching the meshwork—a distance of several millimeters. The $\mu_a$ of water is about 0.022932 (cm$^{-1}$) at 800 nm wavelength. The $\mu_a$ of water at the SLT wavelength of 532 nm is 0.000445 (cm$^{-1}$), which differs by a factor of about 50 from the $\mu_a$ of at 800 nm. The result of this observation is that corneal burns could easily result from the Hsia treatment parameters, particularly since there are anecdotal reports of frequent corneal burns caused by SLT's wavelength—at a much lower $\mu_a$ and much shorter pulse duration.

A principal disadvantage of all prior art approaches described above is by targeting melanosomes in the trabecular meshwork—at low energy levels—any effects are probably limited to surface trabecular sheets. Only the trabecular sheets exposed to the incident beam absorb the beam's photonic energy. This factor suggests that only the first few sheets exposed to the anterior chamber ac are affected by such energy delivery (see FIG. 1A). The deeper meshwork sheets that are likely occluded with debris d (see FIG. 1D) likely remain unaffected by the direct laser irradiation at low power levels. This may explain why IOP can increase after SLT for a period of time in about 20% of patients, which seems to correspond to the time interval necessary for the monocyte/macrophage activity to increase.

None of the laser treatments described above directly target exfoliation debris d that accumulates in the trabecular meshwork and clogs meshwork pores p thereby reducing outflow facility. All of the above treatment modalities target the small volume fraction $f_v$ of melanosomes in meshwork endothelial layers since it is the only endogenous chromophore in the targeted trabecular beams. What is needed is a system and technique for directly delivering ablative energy to cellular detritus and other accumulations within trabecular spaces that will not damage the trabecular cords or meshwork sheets.

SUMMARY OF THE INVENTION

The present invention is adapted to non-invasively apply energy directly to media within spaces in a patient's trabecular meshwork to clear detitrus d that clogs the meshwork to thereby increase aqueous outflow facility. The systems and methods of the invention comprise a combination of (i) an exogenous chromophore introduced into the anterior chamber and localized in the deeper regions of the trabecular meshwork, and (ii) a laser system providing a selected coherent wavelength that is strongly absorbed by the exogenous chromophore particles. This system and method causes photoabsorption of energy by the chromophore nanometric particles, causing thermoelastic expansion therein that propagate bipolar stress waves within the fluid media to cause microcavitation. This localization of microcavitation in fluid that engulfs debris clogging the meshwork spaces can deliver sufficient mechanical energy to ablate the debris without causing significant damage to the trabecular meshwork sheets. In a preferred system embodiment, the chromophore nanocrystalline particles have an average diameter less than about 10–20 nm and are fabricated having a uniformity of dimension, purity level, and sphericity that allows for uniform photoabsorption of the selected coherent wavelength. Recent advances have enabled fabrication of such nanocrystalline particles by means of laser pyrolysis processes described in more detail below.

The systems and methods of the invention stand in clear contrast to all prior art laser irradiation methods that are used to treat the trabecular meshwork as described in the preceding section. All prior art modalities target melanosomes found in trabecular endothelial layers since it is the only endogenous chromophore. For several reasons, such prior art modalities cannot deliver substantial mechanical energy directly to fluids within meshwork spaces to ablate debris—unless very high energy levels are used which in turn would cause substantial damage to the meshwork.

First, all of the above-described prior art methods explode, vaporize or otherwise cause substantial thermal effects in melanosomes—which are embedded in an endothelial layer as depicted in FIG. 1E. At high energy levels in ALT, and at high power levels in the Hsia disclosure, the energy levels explode the melanosome thereby causing cavitation in the interior of the endothelial layer—which cannot be expected to cause any substantial propagation of energy (bipolar stress waves) to fluids at the exterior of the trabecular beams. In contrast, the method of the present invention localizes exogenous chromophores within fluids that engulf the debris clogging the meshwork. Second, the volume fraction ($f_v$) of melanosomes in trabecular epithelial layers is very small, and therefore even high energy levels of that could explode melanosomes would probably result in slight energy propagation to the large volume of fluid media within the meshwork. In contrast, the method of the present invention can localize exogenous chromophores within the aqueous itself at a very high volume fraction ($f_v$) when compared to endogenous melanosomes—the $f_v$ being perhaps greater by a factor of 100 to 1000. The high volume $f_v$ of chromophores also will allow lower fluences to cause the desired microcavitation, that in turn should not cause significant energy absorption by melanosomes. Third, the prior art methods that targeted melanosomes certainly have the highest energy absorption in surface trabecular sheets and endothelial layers that are struck be the laser beam. In contrast, the method of the present invention will localize the exogenous chromophore nanoparticles in deeper levels of the meshwork that are actually clogged with debris, thereby delivering energy directly to site of interest. Fourth, the method of the present invention, since it will not damage or destroy the ultrastructure of the meshwork, can be repeated over the patient's lifetime in a periodic treatment, for example annually or bi-annually which cannot be done with some prior art modalities such as ALT.

In sum, the method of the invention is adapted to cause bipolar stress waves and microcavitation in fluid media surrounding debris d that clogs the patient's trabecular meshwork to ablate such debris. The term debris is used interchangeably in this disclosure with the terms detritus, exfoliations and accumulations to refer to any types of cellular debris, lens flakes, iris pigments or any other materials known to be captured in meshwork pores. This disclosure uses the term ablate interchangeably with the terms disintegrate, obliterate and breakdown to mean the results of energy delivery to the debris that can dimensionally reduce or destroy the debris to allow it to be removed more rapidly form the meshwork via normal aqueous circulation.

The system and technique of the invention advantageously can ablate cellular detritus and other accumulations in a patient's trabecular meshwork by means of energy delivery to exogenous chromophores localized in the meshwork spaces.

The system and technique of the invention provides a non-invasive manner of directly delivering energy to media within meshwork spaces.

The system and technique of the invention treats a patient's trabecular meshwork without targeting and exploding melanosome granules embedded in trabecular endothelial layers.

The invention advantageously provides a volume of photoabsorbing nanoparticles that provide a high volume fraction $f_v$ of chromophores within the region of the debris targeted for ablation.

The system and technique of the invention advantageously provide means for causing greater energy delivery to deeper trabecular sheets rather that surface trabecular sheets.

The system and technique of the invention provides a non-invasive manner of delivering energy to media within meshwork spaces without causing significant thermal effects in the trabecular beams.

The invention advantageously provides a volume of microimplantables comprising nanocrystalline particles having a cross-section of less than about 100 nanometers.

The invention provides a microimplantables of nanocrystalline particles having a uniform dimension and purity to provide uniform energy absorption.

The system and technique of the invention advantageously provides a non-invasive manner of treating the patient's trabecular meshwork in a repeatable maintenance therapy that can continue over the patient's lifetime.

BRIEF DESCRIPTION OF THE DRAWINGS

Other objects and advantages of the present invention will be understood by reference to the following detailed description of the invention when considered in combination with the accompanying Figures, in which like reference numerals are used to identify like elements throughout this disclosure.

DETAILED DESCRIPTION OF THE INVENTION

I. Principles of Laser-Induced Microcavitation of Exogenous Chromophore Particles in Meshwork Spaces.

Figure 4:
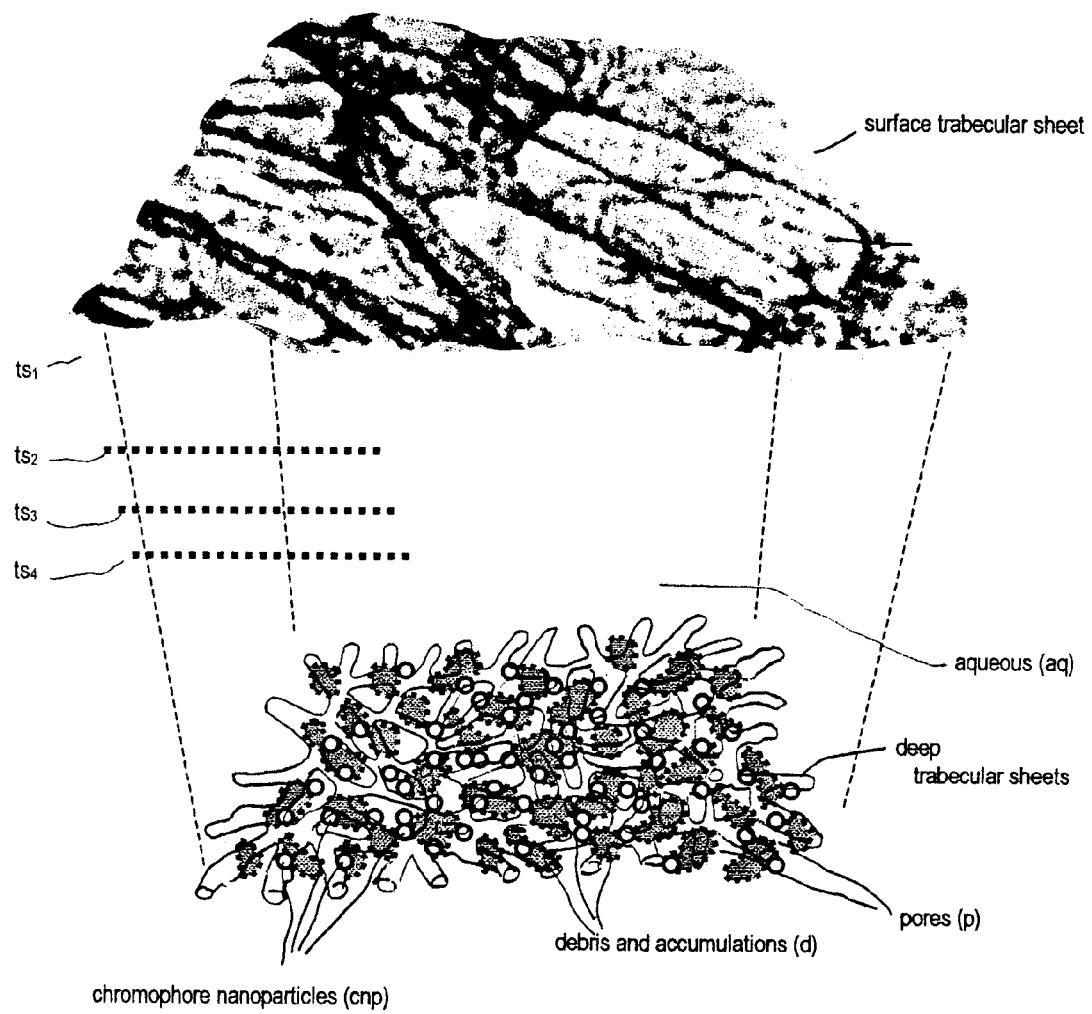
FIG. 4 is a sectional representation of trabecular sheets layers illustrating the localization of exogenous chromophore particles in the fluid media that engulf the debris in the meshwork openings.

The principles relating to method of the invention can be understood from FIG. 4 wherein nanometric particles comprising an exogenous chromophore are introduced into the anterior chamber ac and thereafter transiently accumulate in clogged openings of the trabecular meshwork tm. The chromophore nanometric particles cnp (not to scale) thereafter are irradiated with coherent light to cause microcavitation in the fluid media within the pores p of the meshwork tm thereby delivering mechanical energy to the meshwork region incident to the laser beam.

As background, pulses of coherent light from a laser can deliver energy very rapidly to a targeted media. When the target carries, or comprises, a chromophore that is highly absorbing relative to the selected wavelength, such photoabsorption results in thermoelastic expansion of the target and a rise in internal pressures within the target. The term stress confinement refers to the process of causing an increase in pressure within a targeted media before the pressure can dissipate from the target at the speed of sound. When there exists a defined or free boundary between the targeted media and different surrounding media, such as a liquid or gas interface with the target, the target expands at its surface and then snaps back. The expansion phase is positive pressure or stress and the snap-back is negative stress. When the negative stress exceeds the strength of target media, that media breaks, disintegrates or ejects a surface portion thereof. For example, a laser pulse can that can induce from 20° to 50° C. temperature rises in a targeted composition theoretically can cause transient pressures of from 100–1000 atmospheres to explode the targeted composition.

The same process of laser energy deposition in targeted media can cause the formation of a bipolar positive/negative stress wave that propagates into surrounding media. If the surrounding media were a substantially solid material, the stress wave causes a fracture or break in the material called a spall plane. If the surrounding media were a liquid or a soft tissue, the bi-polar positive/negative stress wave would create cavitation bubbles in the media. In a liquid such as water, when absorbing a selected wavelength, even a slight 4° to 5° C. temperature rise caused by a nanosecond laser pulse can yield a ±10 atm (atmosphere) bipolar stress wave—and the −10 atm negative stress can cause cavitation in water.

The objective of the invention is to localize microcavitation in meshwork spaces to deliver mechanical energy to debris d that clogs the spaces. Of course, water cannot be the target unless a penetrating form of laser energy delivery system is used. Therefore, the invention utilizes a selected exogenous chromophore that is localized by aqueous circulation in the trabecular meshwork to absorb radiation. It is well known that fluid pharmacological agents can be applied to the anterior surface of the cornea c and intra-corneal pressure gradients will transport the agents quite rapidly through the cornea into the anterior chamber ac. The normal circulation of aqueous aq in the anterior chamber will carry the agents about the anterior chamber and eventually to the trabecular meshwork tm as illustrated in FIG. 4. While topical application of a fluid agent carrying exogenous chromophores is preferred, for example in the form of eye drops or migration from an agent-carrying contact lens, it should be appreciated that a needle also may be used to directly introduce chromophore nanoparticles cnp into the anterior chamber. It is believed that chromophore nanoparticles cnp having average diameters of about 10–20 nm or less can be rapidly transported through the cornea c into the anterior chamber, and significantly larger nanoparticles cnp may also pass through corneal lamellae. Still larger particles can be introduced by direct injection into the anterior chamber with a fine needle.

In one embodiment for topical administration, the chromophore nanoparticles cnp have an average diameter less than about 20 nm, wherein the term average diameter means either a diameter of a substantially spherical nanoparticle or the principal (elongate) axis of a less spherical or non-spherical nanoparticle. More preferably, the nanoparticles cnp have an average diameter ranging from about 0.5 nm to 10 nm. For injection into the anterior chamber, the chromophore nanoparticles cnp can have an average cross-section ranging from about 0.5 nm to 100 nm.

The chromophore nanoparticles cnp preferably have a uniformity of dimension, purity, and sphericity thus allowing a selected wavelength of light be absorbed uniformly by all particles. The preferred manner of fabricating the micro-implantables or exogenous chromophore nanoparticles cnp is a manufacturing process called laser pyrolysis developed by NanoGram Corporation, 46774 Lakeview Blvd., Fremont, Calif. 94538. NanoGram Corp. describes its laser pyrolysis process method as a "Nano-Particle Manufacturing" (NPM™) system. The process uses a laser-driven non-equilibrium chemical reaction process in which gases are combined to form simple or complex nanoscale compounds. Aspects of this process are disclosed in U.S. Pat. No. 5,958,348 assigned to NanoGram Corp., which patent is incorporated herein by this reference. NanoGram Corporation's processes are capable of building nanoscale particles from the atomic level to allow for precision nanoparticle sizes, uniformity of shape, as well as nanoparticle purity—all of which will be useful for controlling the parameters of energy delivery within the trabecular meshwork in accordance with the method of the invention. Other manners of chromophore nanoparticle fabrication are possible, such as by a controlled reaction vessel or by machine grinding processes.

Figure 3:
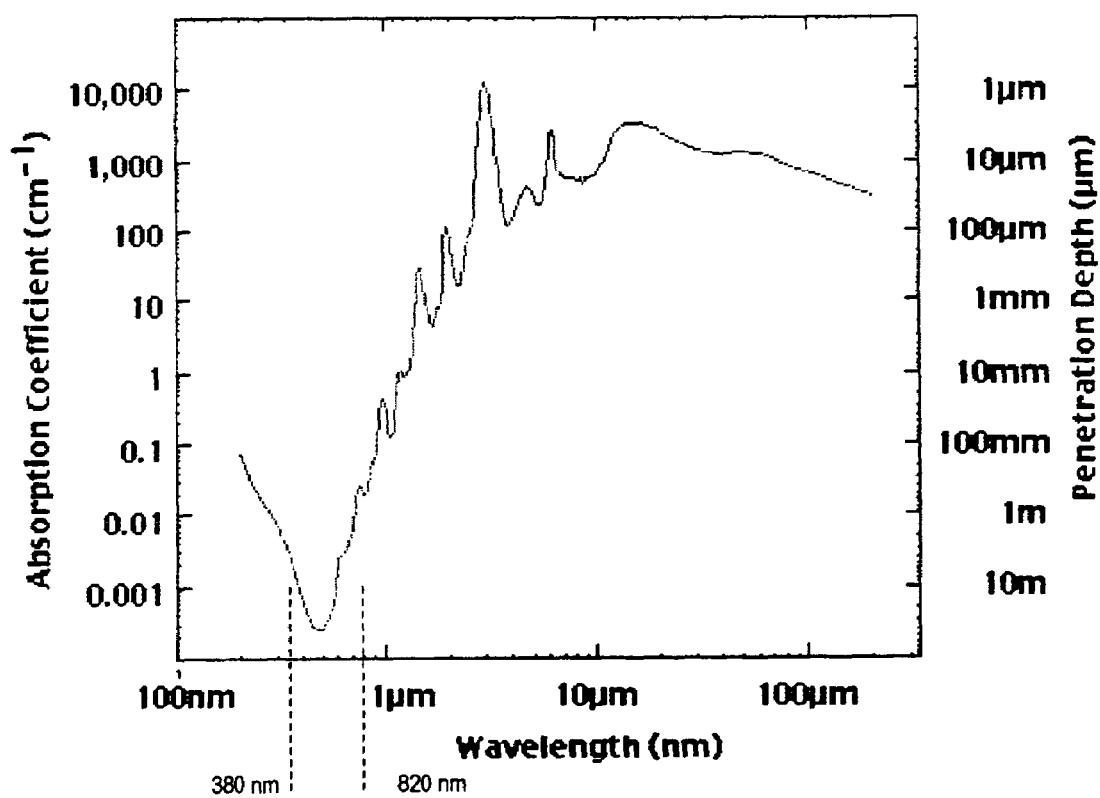
FIG. 3 is a graph showing the absorption coefficient of water over a wavelength spectrum.

II. Exemplary Chromophore Nanoparticles and Absorption Coefficients for Energy Delivery Via Microcavitation For practicing the method of the invention in a non-invasive manner, a selected wavelength (λ) must not be significantly absorbed by water. FIG. 3 is a graph of absorption coefficients $\mu_a$ ($cm^{-1}$) for water across a wavelength spectrum which can be used for modeling purposes since the cornea c and aqueous aq are about equivalent to water. The preferred wavelengths (λ) are preferably below about 820 nm. that will allow short pulse laser trans-corneal irradiation to reach the region of the meshwork without significant thermal effects in the intervening media, particularly the cornea c. More preferably, the wavelength is below about 650 nm. Still more preferably, the wavelength is below about 550 nm. The wavelengths are preferably well above the ultraviolet range in which energies level are high and have been investigated for having mutagenic effects.

Figure 1A:
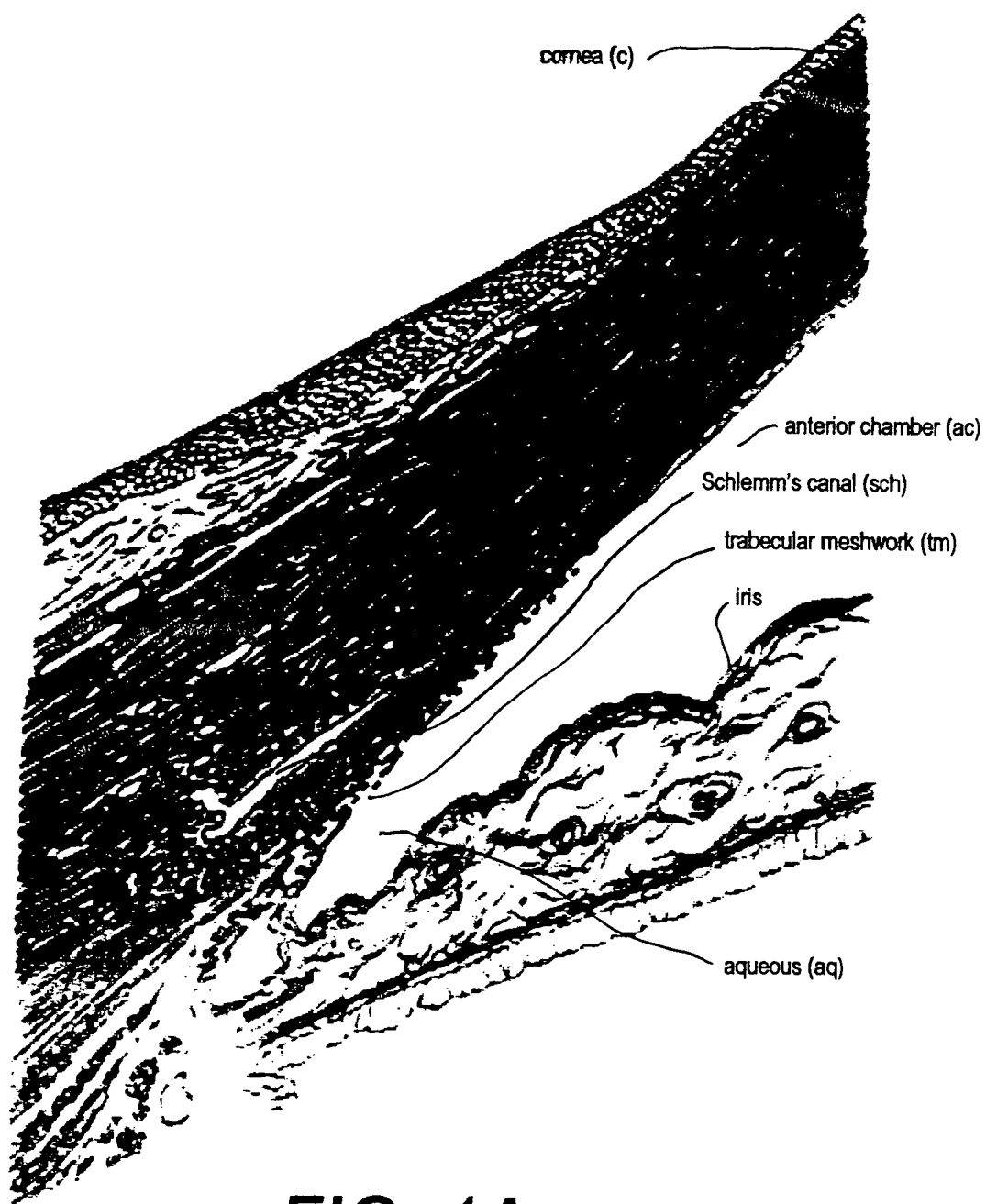
FIG. 1A is a sectional view of a patient's eye showing the location of the trabecular meshwork.
Figure 1B:
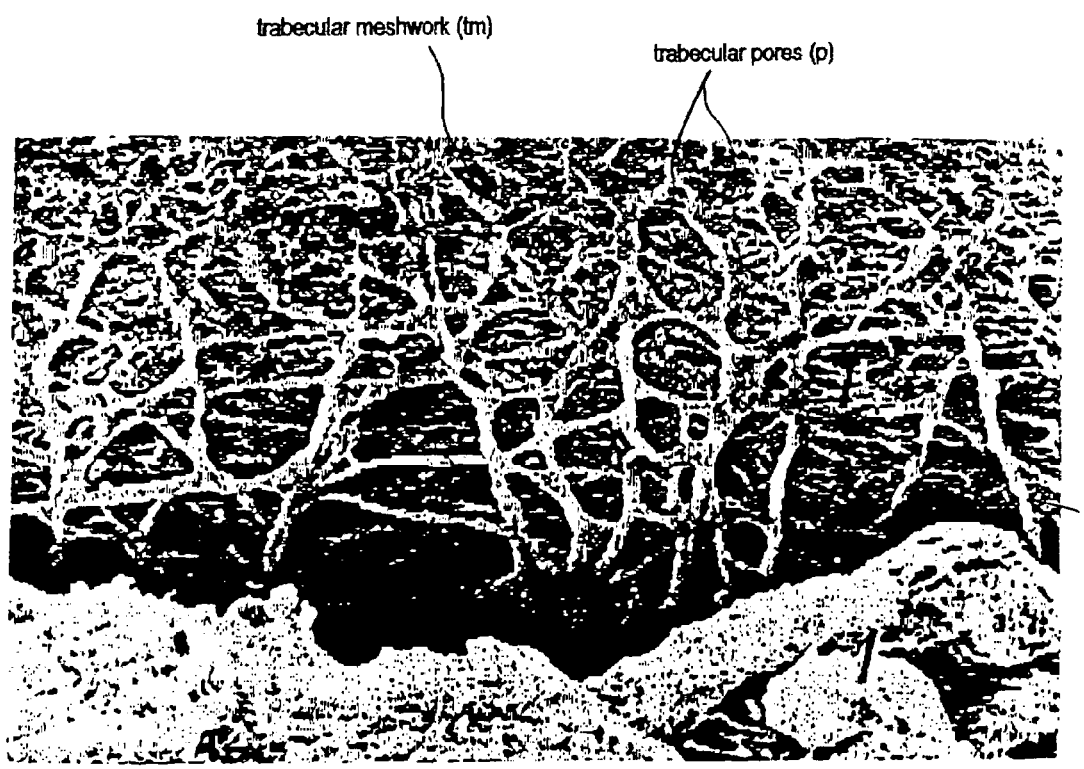
FIG. 1B is an electron micrograph of the trabecular meshwork of a patient's eye.
Figure 1C:
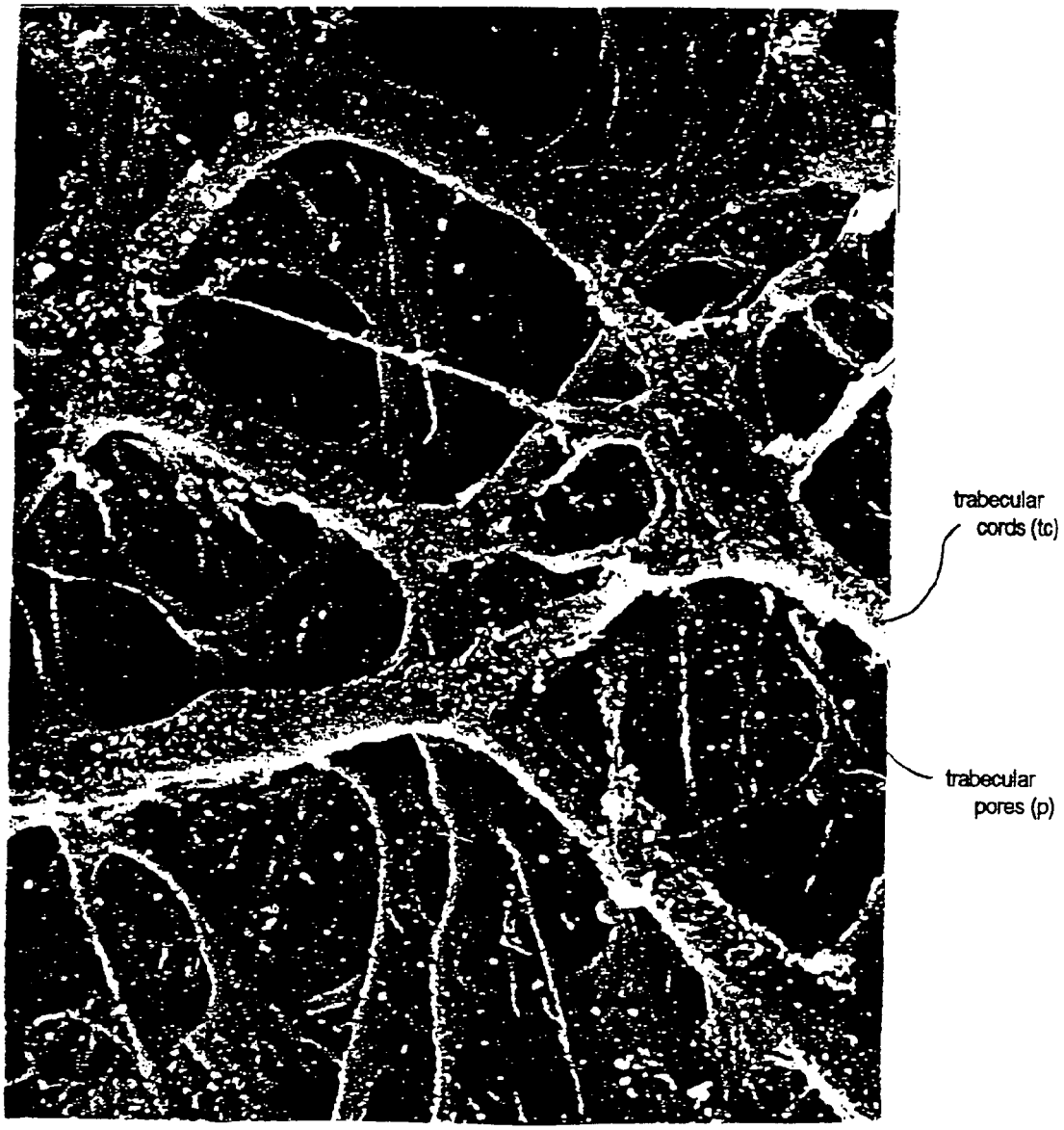
FIG. 1C is an enlarged electron micrograph of the trabecular meshwork of FIG. 1B.
Figure 1D:
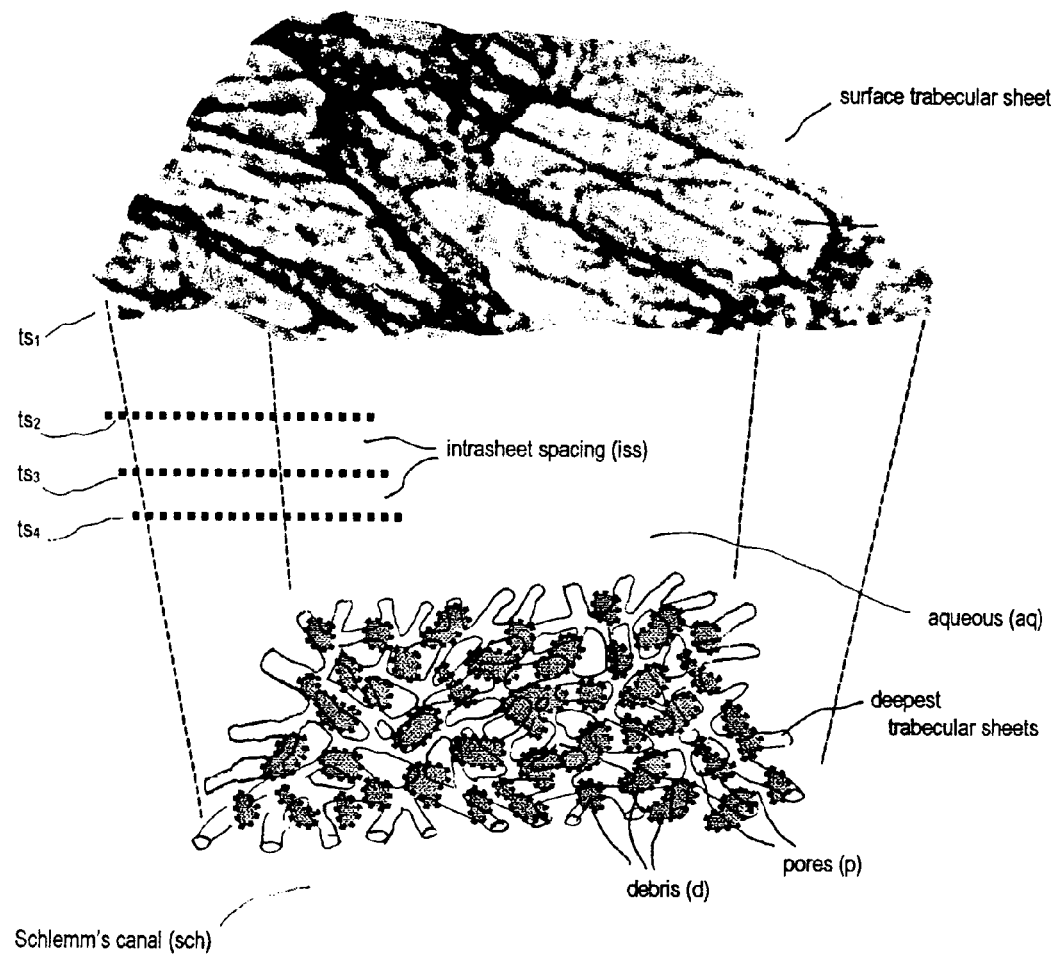
FIG. 1D is a sectional representation of the trabecular plate layers of meshwork of FIG. 1A showing debris and accumulations in the deeper meshwork sheets.
Figure 1E:
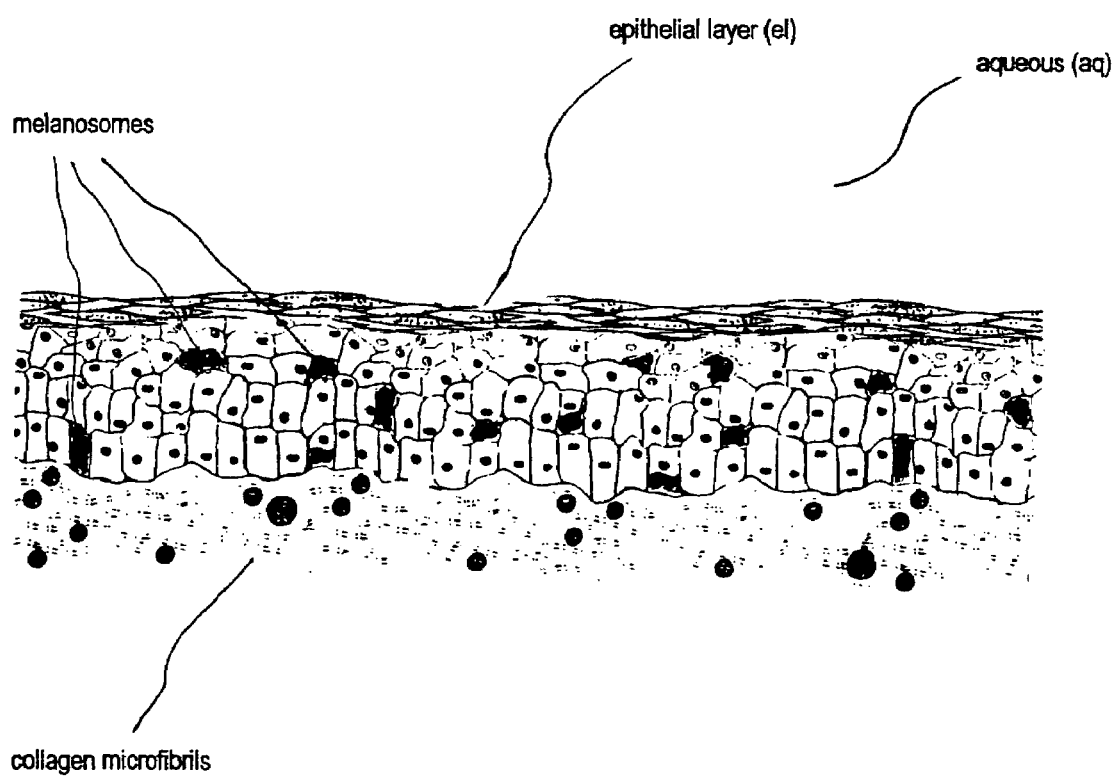
FIG. 1E is a graphic illustration of naturally-occurring melanosome organelles in a trabecular endothelial layer indicating the small volume fraction ($f_v$) of the chromophore.
Figure 2:
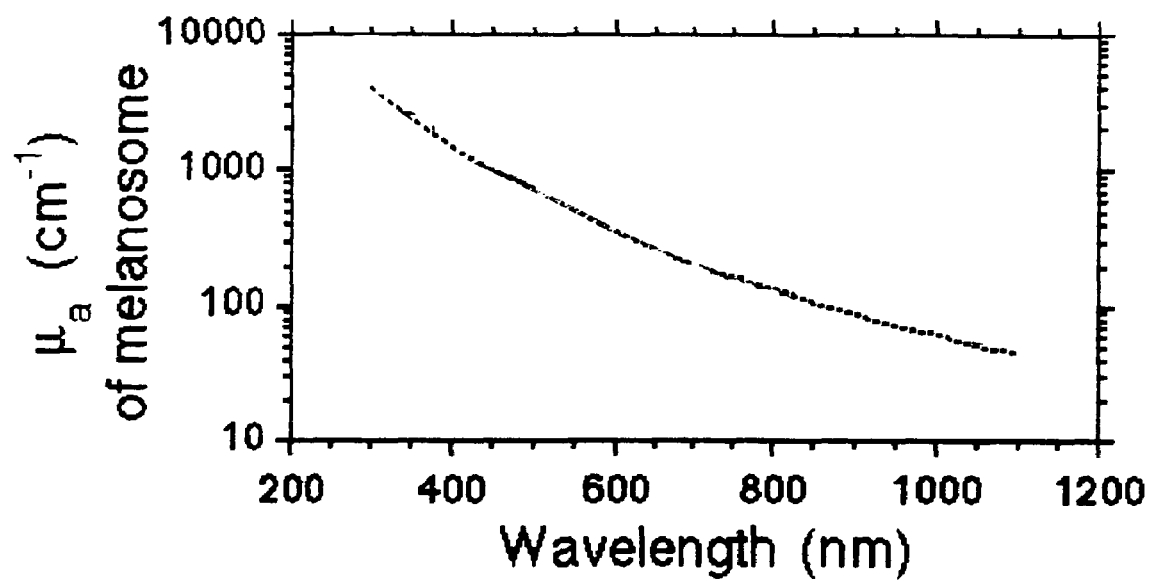
FIG. 2 is a graph showing the absorption coefficient of melanin over a wavelength spectrum.

For any selected wavelength within the above range, the chromophore is selected one the basis of its absorption coefficient so that it is strongly absorbing. The following sections describe exemplary chromophores that can comprise, or be carried by, the implantable nanometric particles of the invention and the spectral range for which they are best suited, commencing with chromophore that are strongly absorbing in preferred lower wavelength ranges from about 380 nm to 650 nm, and proceeding to the less preferred (longer wavelength) ranges. The chromphores are further selected to have a high absorption coefficient ($\mu_a$) at a selected wavelength relative to the $\mu_a$ of melaonsomes on the trabecular endothelial layer (cf. FIG. 2). Thus, by having a high $f_v$ (volume fraction) and high $\mu_a$ of exogenous chromophore particles in trabecular spaces, compared to the $f_v$ and $\mu_a$ of endogenous melanosome chromphores embedded in epithelial layers, low power levels and fluences can cause the energy photoabsorption required for microcavitation while still not causing significant effects in the meshwork epithelial layers.

A. Chromophore nanoparticles of iron or equivalents. Biocompatible pure iron (Fe) can serve as a suitable chromophore. Iron can be fabricated into nanoparticles having uniform diameters of about 0.5 nm to 10 nm and can be introduced into the meshwork via transportation through the cornea in a topical administration or by direct injection into the anterior chamber ac. Direct injection of larger particles is possible, for example nonoparticles up to 100 nm in diameter. NanoGram Corp. has used laser pyrolysis to synthesize iron nanoparticles. For several reasons, the absorption coefficient ($\mu_a$) peaks for iron-carrying nanoparticles are not certain, although estimates can be made since hemoglobin is a commonly targeted chromophore in photothermolysis techniques for treating port wine stains. NanoGram Corp. has found that some nanoparticles (e.g., a titanium oxide ($TiO_2$)), when fabricated in particle sizes below a certain critical value, have an optical absorption band that shifts leading to different absorption peaks. This property can be useful to improve the performance of nanoparticles when functioning as a chromophore. It is not known at this time whether iron nanoparticles of the preferred dimensions will shift $\mu_a$ peaks, or why the $\mu_a$ shifts. The best estimates of the $\mu_a$ for Fe when taken from investigations of hemoglobin spectra are further complicated by the fact that values are typically tabulated by various "equivalents" that contain 1 gm atom of Fe that combines with 1 gm molecule of either $O_2$ or CO. In any event, such hemoglobin equivalents have one absorption peak at about 400 nm and another lower peak at about 520–550 nm. Using hemoglobin as a proxy for pure Fe chromophore nanoparticles cnp is still reasonable, and the method of the invention can generalize the use of wavelengths ranging from about 380 nm to 550 nm to absorb non-invasively delivered laser energy.

The effects on the nanoparticles are described above and can result in microcavitation to ablate debris d captured in the trabecular meshwork without causing gross damage to the trabecular sheets or cords. NanoGram Corp. has also fabricated and characterized iron oxides nanocrystals and the use of any such iron oxides fall within the scope of the invention. It is believed that the $\mu_a$ peaks for such iron oxides will be similar to Fe but further testing is required.

After introduction of the chromophore nanoparticles cnp into the anterior chamber, the ophthalmologist waits a period of time ranging from about 2 to 10 minutes to allow the nanoparticles to accumulate among debris d within the meshwork as depicted in FIG. 4. The particle size may be selected to insure that they do not rapidly migrate through the meshwork pores p. The ophthalmologist delivers the laser beam gonioscopically, and a lower power aiming beam also can be used as is known in the art. The spot size can be from about 100 µm to 500 µm diameters, preferably being about 200 µm to 400 µm in diameter, to substantially cover the width of the meshwork at the incident angle. A suitable series of overlapping or adjacent spots can be delivered around 360° of the meshwork. The preferred pulse duration is estimated to be from about 10 ps to 1.0 microsecond to deliver from about 1 mJ/pulse to 100 mJ/pulse. The actual selected energy delivery parameters will be the minimum energy required to cause energy deposition in the chromophore nanoparticles cnp that, in turn, will propagate bipolar stress waves capable of causing microcavitation in fluid media within the meshwork pores. The microcavitation thereby delivers energy to the debris d and accumulations in the meshwork to ablate these materials.

B. Fluorescein chromophores and nanoparticles. Biocompatible fluorescein compositions are suited for practicing the method of invention. Fluorescein has been found to have varied peaks in $\mu_a$ depending on the manner of testing, for example at 482.5 nm (see P. G. Seybold, M. Gouterman, & J. Callis, *Calorimetric, photometric and lifetime determinations of fluorescence yields of fluorescein dyes, Photochem. Photobiol.* 9, 229–242 (1969)); or from 484 nm 520 nm in various solutions (see M. M. Martin, *Hydrogen bond effects on radiationless electronic transitions in xanthene dyes, Chem. Phys. Lett.* 35, 105–111 (1975)). When measuring absorption by fluorescence maximums, the peaks have been found to shift from between 508 nm to 543 nm depending on solutions (see M. M. Martin, *Hydrogen bond effects on radiationless electronic transitions in xanthene dyes, Chem. Phys. Lett.* 35, 105–111 (1975)). Thus, the combination of coherent wavelengths ranging between about 450 nm and 550 nm and fluorescein chromophores introduced into a patient's trabecular meshwork via topical administration is one preferred system combination for practicing the method of the invention. The power level, pulse duration and repetition rate would be adjusted to determine the selected parameters that cause microcavitation as described above. In a preferred embodiment, the chromophore composition comprises fluorescein that is manufactured in uniformly-sized nanoparticles, either in combination with a binder element that is non-absorbing at the selected wavelengths or alone, using the laser pyrolysis methods of NanoGram Corp. described above. These chromophore nanoparticles cnp preferably have the dimensions and characteristics described above—most preferably being substantially spherical in shape with a uniform average diameter from about 0.5 nm to 20 nm.

It should be appreciated that fluorescein chromophores fall within a class sometimes referred to as xanthene compositions and such compositions as a class have absorption peaks between about 480 nm and 580 nm and any such xanthene compositions fall within the scope of the invention. For example, rose bengal is another biocompatible composition that has an absorption peak at 559 nm.

C. Chromophore nanoparticles of carbon. Carbon in the form of chromophore nanocrystalline particles having uniform diameters ranging from about 0.5 nm to 10 nm can be used in the method of the invention. Such nanoparticles can be introduced into the meshwork via direct injection or possibly by transportation through the cornea in a topical administration. NanoGram Corp. has fabricated and characterized such carbon nanocrystals. The $\mu_a$ for carbon is believed to be without sharp peaks across the preferred spectrum with higher absorptions at shorter wavelengths. The method of the invention can generalize the use of wavelengths ranging from about 450 nm to 600 nm to cause photomechanical energy effects in carbon nanoparticles.

In order to create chromophore nanocrystalline particles cnp that remain in solution for dispersed introduction into the meshwork pores, the chromophore particles may be coated with any suitable coating that prevents the chromophore particles from reacting with one another. For example, the chromophore nanocrystalline particles can be encapsulated in a liposome as is known in the art. Other coating processes are being investigated, for example, the use resorcinarenes has been investigated for coating elemental metals ands should be suitable for coating carbon, iron or other chromophores referenced herein. In some chromophore nanocrystalline particles described above, a biocompatible binder material is used to assemble with the selected chromophore to provide the selected particle dimension. The binder may be any suitable binder commonly used in pharmacological compositions.

D. Methylene blue chromophores and nanoparticles. Methylene blue ($C_{16}H_{18}ClN_3S$) is an agent that has been investigated for use in topical treatments for photodynamic therapies as well as use as a surgical dye (see, e.g., K. Heckelsmiller, et al., *Nonlinear dynamics of intracellular methylene blue during light activation of cell cultures, Photochem. Photobiol.* 66, 837 (1997)). The absorption peaks are at about 668 nm and 609 nm, and a wavelength range between about 580 nm and 700 nm would be suitable for photoabsorption induced propagation of bipolar stress waves as described previously. This chromophore can be combined with any suitable binder and fabricated in the preferred dimensions described above.

Methylene blue also can be activated by in the wavelength range referenced above to an excited state that in turn will activate oxygen to yield oxidizing radicals. It is known that such radicals can cause crosslinking of amino acid residues on certain proteins, and for this reason has been investigated in the field of photochemical-enhanced tissue welding. The scope of the method of the invention includes the photosensitizing of suitable chromophores (e.g., methylene blue) to cause such radicals which it is believed will then induce the body's wound healing response—thereby recruiting macrophages to help clean debris from the trabecular meshwork as described above in the Section titled "Description of Related Art."

Methylene blue also has derivatives called azure A, B, C and thionine which fall into a class sometimes referred to a phenothiazine compositions or dyes which all fall within the scope of the invention. These photoactive agents are biocompatible and have been investigated for photodynamic virus inactivation of blood products (see, e.g., H. Mohr, B. Bachmann, A. Klein-Struckmeier, B. Lambrecht, *Virus inactivation of blood products by phenothiazine dyes and light, Photochem. Photobiol.* 65, 441 (1997)).

E. Tricarbocyanine chromophores and nanoparticles. A tricarbocyanine composition has suitable photoabsorption properties, for example indocyanine green or ICG ($C_{43}H_{47}N_2O_6S_2Na$) that has absorption peaks in a water solution at 700 nm and about 800 nm. ICG is known to be biocompatible and has been used diagnostically for determining blood volume, cardiac output, and hepatic functions. Additionally, ICG has been found to have very low toxicity, and is rapidly excreted into the bile. ICG has been used extensively in laser tissue welding because of its absorption properties at a common laser diode wavelength of about 800 nm. ICG in a water solution has odd $\mu_a$ characteristics since its absorption peaks shift as a function of concentration in water, and ICG particles have been found to aggregate at high concentrations. It is not likely that ICG concentrations in aqueous aq will alter its effective absorption. The method of the invention can generalize the use of wavelengths ranging from about 680 nm to 820 mm to cause the desired photoabsorption effects in chromophore nanoparticles. The laser energy delivery parameters described previously can be used with ICG particles to cause microcavitation to ablate debris in the trabecular meshwork while at the same time not causing biostructural changes in the trabecular sheets or cords. The preferred pulse duration for wavelengths in the 800 mm range is short or ultrashort, and a Ti:Sapphire laser can be used to deliver pulses as short as about 20 fs.

A number of laser types known in the art are suitable for providing the required wavelengths, power levels and pulse durations described above. For some wavelengths in the 740–820 nm range in which a short or ultrashort pulse is optimal, a suitable Ti:Sapphire laser is available from Pico-Quant GmbH, Rudower Chaussee 29 (IGZ), 12489 Berlin, Germany (http://www.picoquant.com).

In another system and method of the invention, the microimplantable can consist of a gold particle or gold nanoshell that is injected into the anterior chamber or directly into the meshwork. In one embodiment, the gold nanoparticle can be irradiated with Ti:Sapphire laser as described above that produces wavelengths in the 740–820 nm range.

In another embodiment, the gold nanoshells can be of a new type with an optically tunable ultra-thin metallic (for example, gold) surface layer. Gold nanoshells are available from Nanospectra Biosciences, Inc., 8285 El Rio Street, Suite 130, Houston, Tex. 77054. The physical properties of gold nanoshells are similar to gold colloid and exhibit a strong optical absorption due to the collective electronic response of the metal to light. The optical response of gold nanoshells depends on relative sizes of the nanoparticle cores and the thickness of the gold shell. It ahs been found that by varying the relative core and shell thicknesses, the color of gold nanoshells can be varied across a broad range of the optical spectrum that spans the visible and the near-IR spectral regions to either to absorb or scatter light. The gold nanoshells also can carry a drug that can be eluted therefrom in response to optical absorption. The method of the invention thus includes irradiating a volume of gold particles or nanoshells localized within the meshwork, wherein optical absorption of energy by the particles applies enhanced energy to the irradiated region of the meshwork.

Those skilled in the art will appreciate that the exemplary systems, combinations and descriptions are merely illustrative of the invention as a whole, and that variations in the composition and dimensions of the chromophore particles, and the cooperating wavelengths, power levels, pulse durations and pulse intervals may be made within the spirit and scope of the invention. Specific characteristics and features of the invention and its method are described in relation to some figures and not in others, and this is for convenience only. While the principles of the invention have been made clear in the exemplary descriptions and combinations, it will be obvious to those skilled in the art that modifications may be utilized in the practice of the invention, and otherwise, which are particularly adapted to specific environments and operative requirements without departing from the principles of the invention. The appended claims are intended to cover and embrace any and all such modifications, with the limits only of the true purview, spirit and scope of the invention.

What is claimed is:

1. A method for treating trabecular meshwork regions of a human eye, comprising the steps of:
   (a) localizing a volume of particles carrying a selected chrontiophore within spaces of the meshwork;
   (b) irradiating the particles with a beam of photonic energy having a wavelength, power, and pulse duration that is absorbed by the selected chromophore;
   (c) wherein the chromophore comprises gold within the surface layer of said particles thereby applying energy to the irradiated region of the meshwork.

2. The method of claim 1 wherein the irradiating step causes a thermal effect within the irradiated region of the meshwork.

3. The method of claim 1 wherein the irradiating step causes a cavitation effect within the irradiated region of the meshwork.

4. The method of claim 3 wherein said cavitation delivers mechanical energy to a media within the meshwork.

5. The method of claim 1 wherein the particles have an average diameter of less than about 500 nm.

6. The method of claim 1 wherein the particles have an average diameter less than about 200 nm.

7. The method of claim 1 wherein the irradiating step utilizes a wavelength domain ranging from about 380 nm to 820 nm.

8. A method for applying energy to a patient's trabecular meshwork, comprising the steps of:
   (a) localizing microimplantables with a gold surface within spaces of the meshwork;
   (b) non-invasively irradiating the meshwork region with coherent light pulses having a wavelength between 380 nm and 820 nm;
   (c) wherein the power level, pulse, and pulse interval are selected to cause the microimplantables to absorb energy and thereby apply energy to surrounding media.

9. The method of claim 8 wherein said irradiating step causes thermal effecis in said media.

10. The method of claim 8 wherein said irradiating step cause acoustic effects in said media.

11. The method according to claim 8 wherein said irradiating step does not ablate cells of the meshwork.

* * * * *

UNITED STATES PATENT AND TRADEMARK OFFICE
CERTIFICATE OF CORRECTION

PATENT NO. : 6,989,007 B2  Page 1 of 1
APPLICATION NO. : 10/765482
DATED : January 24, 2006
INVENTOR(S) : John H. Shadduck It is certified that error appears in the above-identified patent and that said Letters Patent is hereby corrected as shown below:

Column 2,
Line 42, delete "A" and insert --$\lambda$--

Column 6,
Line 8, delete "inte" and insert --interior--

Column 6,
Line 57, delete "monocytelmacrophage" and insert --monocyte/macrophage--

Column 15,
Line 38, delete "ahs" and insert --has--

Column 16,
Line 16, delete "chrontiophore" and insert --chromophore--

Column 16,
Line 50, delete "effecis" and insert --effects--

Signed and Sealed this

Thirtieth Day of January, 2007

JON W. DUDAS
*Director of the United States Patent and Trademark Office*